US008080686B2

(12) United States Patent
Benderly et al.

(10) Patent No.: US 8,080,686 B2
(45) Date of Patent: Dec. 20, 2011

(54) INTEGRATED PROCESS FOR PREPARING A CARBOXYLIC ACID FROM AN ALKANE

(75) Inventors: Abraham Benderly, Elkins Park, PA (US); Nitin Chadda, Radnor, PA (US); Douglass Sevon, Fairless Hills, PA (US)

(73) Assignee: Rohm and Haas Company, Philadelphia, PA (US)

( * ) Notice: Subject to any disclaimer, the term of this patent is extended or adjusted under 35 U.S.C. 154(b) by 233 days.

(21) Appl. No.: 12/316,322

(22) Filed: Dec. 11, 2008

(65) Prior Publication Data

US 2009/0171109 A1    Jul. 2, 2009

Related U.S. Application Data

(60) Provisional application No. 61/009,118, filed on Dec. 26, 2007.

(51) Int. Cl.
*C07C 51/16* (2006.01)
*C07C 57/02* (2006.01)

(52) U.S. Cl. ......... 562/545; 562/546; 562/547; 562/598

(58) Field of Classification Search .................. None
See application file for complete search history.

(56) References Cited

U.S. PATENT DOCUMENTS

| | | | |
|---|---|---|---|
| 4,046,833 | A | 9/1977 | Hardman |
| 5,705,684 | A | 1/1998 | Hefner et al. |
| 6,239,325 | B1 | 5/2001 | Kishimoto et al. |
| 2003/0187299 | A1* | 10/2003 | Machhammer et al. ...... 562/547 |
| 2005/0085678 | A1 | 4/2005 | Lopez Nieto et al. |
| 2005/0124840 | A1 | 6/2005 | Chen et al. |

FOREIGN PATENT DOCUMENTS

| | | |
|---|---|---|
| EP | 0117146 B1 | 8/1984 |
| EP | 1112241 B1 | 2/2003 |
| EP | 1 916 230 A | 4/2008 |
| WO | WO 2004/054945 | 7/2001 |
| WO | WO 01/96271 A | 12/2001 |

OTHER PUBLICATIONS

White et al, Basic Energy Sciences Advisory Committee Subpanel Workshop Report, Opportunities for Catalysis in the 21st Century, 2002, pp. 1-47.*
Zhaorigetu, B., et al., "Oxidative Dehydrogenation of Propane on Rare Earth Vanadates. Influence of the Presence of CO2 in the feed." Studies in Surface Science and Catalysis, 1996, vol. 101, pp. 1049-1058.
Li, X.-H.,et al., "Supported Vanadia Catalysts for Dehydrogenation of Ethylbenzene with CO2," Catalyst Letters, Dec. 2005, vol. 105, Nos. 3-4.
Dury, F.; et al., "The Active Role of CO2 at Low Temperature in Oxidation Processes: The Case of the Oxidative Dehydrogenation of Propane on NiMoO4 catalysts," Applied Catalys, Catalysis A: General, 2003, vol. 242, pp. 187-203.
Takehira, K.; et al., "CO2 Dehydrogenation of Propane over Cr-MCM-41 Catalyst," Studies in Surface Science and Catalysis, 2004, 153, 323-328.

* cited by examiner

*Primary Examiner* — Paul A Zucker
(74) *Attorney, Agent, or Firm* — Marcella M. Bodner (57) ABSTRACT

The present invention relates to an integrated process for producing unsaturated carboxylic acids from the corresponding $C_2$-$C_4$ alkane. The process begins with performance of thermally integrated dehydrogenation reactions which convert a $C_2$-$C_4$ alkane to its corresponding $C_2$-$C_4$ alkene, and which involve exothermically converting a portion of an alkane to its corresponding alkene by oxidative dehydrogenation in an exothermic reaction zone, in the presence of oxygen and a suitable catalyst, and then feeding the products of the exothermic reaction zone to an endothermic reaction zone wherein at least a portion of the remaining unconverted alkane is endothermically dehydrogenated to form an additional quantity of the same corresponding alkene, in the presence of carbon dioxide and an other suitable catalyst. The alkene products of the thermally integrated dehydrogenation reactions are then provided to a catalytic vapor phase partial oxidation process for conversion of the alkene to the corresponding unsaturated carboxylic acid or nitrile. Unreacted alkene and carbon dioxide are recovered from the oxidation product stream and recycled back to the thermally integrated dehydrogenation reactions.

10 Claims, 3 Drawing Sheets

INTEGRATED PROCESS FOR PREPARING A CARBOXYLIC ACID FROM AN ALKANE

This application claims the benefit of priority under 35 U.S.C. §119(e) of U.S. Provisional Patent Application No. 61/009,118, filed on Dec. 26, 2007.

GOVERNMENT INTEREST

This invention was made with Government support under Instrument No. DE-FC36-O4GO14272 awarded by the United States Department of Energy. The Government has certain rights in this invention.

FIELD OF THE INVENTION

The present invention relates to an integrated process for preparing a carboxylic acid from its corresponding alkane utilizing an energy efficient catalyzed dehydrogenation step to produce the corresponding alkene, followed by partial oxidation of the alkene to produce the carboxylic acid.

BACKGROUND OF THE INVENTION

Well-known commercial processes for the production of monomers, such as unsaturated carboxylic acids and unsaturated nitriles, typically start with one or more alkenes and convert them, by catalytic vapor phase oxidation, to the desired monomer products. In view of the pressures exerted by competition in the industry, and the price difference between alkanes and their corresponding alkenes, such as propane and propene, respectively, efforts are being made to develop processes in which an alkane is used as the starting material to, ultimately, produce the desired monomers at a lower overall cost.

One process modification, which has enjoyed some success in commercial industry, is to simply add an upstream reaction stage in which an alkane is first converted to the corresponding alkene, in the presence of a suitable catalyst. The resulting alkene (e.g., propene) is then fed to the customary oxidation reaction stages, for oxidation of the alkene (e.g., first to acrolein and then to the desired monomer product, as in the two-step oxidation of propene to form acrylic acid). For example, both European Patent Application No. EP0117146 and U.S. Pat. No. 5,705,684 describe multi-stage catalytic processes for converting an alkane (propane) to the corresponding unsaturated carboxylic acid (acrylic acid) which includes an initial alkane-to-alkene conversion stage having one or more suitable catalysts to produces a product stream comprising alkene, which is fed to one or more downstream oxidation stages. Various catalysts and methods are known to catalyze conversion of alkanes to their corresponding alkenes.

For example, mixed metal oxide catalysts having, as essential elements, Mo—Sb—W or Cr—Sb—W, and at least one metal selected from the group consisting of V, Nb, K, Mg, Sn, Fe, Co and Ni, were shown to be useful for oxidative dehydrogenation of propane to produce propene, in single-pass yields of greater than 10% (U.S. Pat. No. 6,239,325). A Pd—Cu/Mn catalyst on zirconium oxide support also catalyzed the oxidative dehydrogenation of ethane, with selectivities to ethane in the range of 70%-80% and diminished coke formation (US Patent Application Publication No. 2005/0124840). Furthermore, oxidative dehydrogenation of ethane in the presence of an Mo—V—Te—Nb-based mixed metal oxide catalyst has been shown to produce ethene in yields as high as 50%, and, in one case, even greater than 60% (US Patent Application Publication No. 2005/0085678). A vanadium-aluminum based mixed metal oxide catalyst, with or without one or more additional metal oxides of Cr, Zn, Fe and Mg, is known to be capable of catalyzing the conversion of propane, n-butane, isobutane, isopentane to their corresponding alkenes, in the presence of oxygen, to achieve relatively high alkene selectivities while minimizing the formation of coke and, thereby, minimizing the need for catalyst regeneration (U.S. Pat. No. 4,046,833). Zhaorigetu, et al. (1996) demonstrated that oxidative dehydrogenation of propane over an unsupported vanadium-based catalyst promoted with one or more rare earth metals (La, Ce, Pr, Sm and Er) could be enhanced by providing carbon dioxide, in addition to oxygen, to the reaction zone (Zhaorigetu, B.; Kieffer, R.; Hinderman J.-P., "Oxidative Dehydrogenation of Propane on Rare Earth Vanadates. Influence of the Presence of CO2 in the feed." *Studies in Surface Science and Catalysis*, 1996, 101, 1049-1058).

Since it is exothermic, when an oxidative dehydrogenation process is operated continuously, excess heat must be continuously removed, which increases capital and operating expenditures. Another disadvantage of oxidative dehydrogenation is that selectivity to alkene tends to decrease when the process is operated at higher, commercially useful alkane conversion rates. Thus, in practice, these processes tend to be operated at lower conversion rates (well below 100%), which limits their product yield capacity and generally renders them economically unsuitable for use in commercial-scale processes.

Other catalysts are known to catalyze the endothermic dehydrogenation of an alkane, in the presence of a "weak" oxidant, such as steam or carbon dioxide, to form the corresponding alkene. Some endothermic dehydrogenation catalysts perform better in the absence of oxygen, while others tolerate the presence of minor amounts of oxygen, along with the weak oxidant, without significant loss of activity. Supported vanadium-based catalysts, promoted with Li, Na, K or Mg, have been shown to dehydrogenate ethylbenzene in the presence of a "soft oxidant," i.e., carbon dioxide, to produce styrene with selectivities of about 98-99%, in the absence of oxygen (Li, X.—H.; Li, W.—Y.; Xie, K.—C., "Supported Vanadia Catalysts for Dehydrogenation of Ethylbenzene with CO2," *Catalyst Letters*, December 2005, Vol. 105, Nos. 3-4). Carbon dioxide was provided in varying amounts by Dury, et al. in 2002 to the oxidative dehydrogenation of propane to form propene in the presence of nickel-molybdenum-based catalysts, and found to increase conversion (by about 18-28%) but decrease selectivity (Dury, F.; Gaigneaux, E. M., Ruiz, P., "The Active Role of CO2 at Low Temperature in Oxidation Processes: The Case of the Oxidative Dehydrogenation of Propane on NiMoO4 catalysts," *Applied Catalysis A: General* 242 (2003), 187-203). Dury et al. demonstrated that, contrary to the traditional expectation that carbon dioxide is inert in dehydrogenation reactions, carbon dioxide actively participates in the dehydrogenation of propane, even in the absence of oxygen. Takehira, et al. tested the activities of various metal oxide catalysts (Cr, Ga, Ni, V, Fe, Mn and Co) supported on silicon-containing support materials, including mesoporous MCM-41, Cab-O-Sil, and silicon oxide, and found that the Cr-based catalyst supported on MCM-41 provided the best results for dehydrogenation of propane, in the presence of carbon dioxide, to form propene. Takehira, K.; Oishi, Y.; Shishido, T.; Kawabata, T.; Takaki, K.; Zhang, O.; and Wang, Y., "CO2 Dehydrogenation of Propane over Cr-MCM-41 Catalyst," *Studies in Surface Science and Catalysis*, 2004, 153, 323-328.

Obviously, endothermic dehydrogenation processes require addition of heat to the process. They typically involve burning (i.e., combusting) a hydrocarbon fuel, often different than the alkane to be dehydrogenated, with oxygen in a furnace or other vessel, resulting in increased costs due to increased initial capital investment and ongoing fuel consumption.

European Patent Application Publication No. EP 1112241 ("EP '241") describes a process designed to address this issue. Rather than burning a separate fuel to produce heat, the disclosed process involves combusting a portion of the alkane which is to be dehydrogenated, with oxygen, in the presence of a suitable combustion catalyst, to produce a heated stream containing the products of combustion (i.e., carbon oxides and water), unconsumed oxygen and unconsumed alkane. The heated stream is fed directly to an endothermic catalytic dehydrogenation reaction stage where the unreacted alkane is converted to the corresponding alkene in the presence of a suitable dehydrogenation catalyst.

More recently, International Patent Application Publication No. WO 2004/054945 ("WO '945") provides an improvement to the aforesaid two-stage exothermic-endothermic process, which eliminates the need for the combustion catalyst by substituting an ignition source, such as a pilot flame or a spark ignition, and burning a portion of the alkane to produce a heated stream comprising unreacted alkane, and either products of combustion (i.e., carbon oxides, water and heat), or synthesis gas (i.e., carbon monoxide and hydrogen).

Thus, in the processes of both EP '241 and WO '945, the need to burn a separately provided hydrocarbon fuel to preheat the alkane feed is avoided. However, a portion of the alkane reactant is consumed, which leaves less available for conversion to the desired product in the dehydrogenation stage. Furthermore, products of combustion are incidentally formed, which increases the amount of unwanted by-products, without any contribution to the quantity of the desired alkene product. In fact, when a portion of the alkane reactant itself is burned, as taught by these sources, a diminished amount of alkane remains available for the dehydrogenation reaction and less of the desired alkene product is produced.

Accordingly, notwithstanding the work conducted to date in this field, industry continues to grapple with the aforesaid problems of increasing overall production of alkene (i.e., increasing alkene selectivity and yield), while minimizing the costs of dehydrogenation of lower alkanes to their corresponding alkenes. Development of an improved process and catalyst system for converting an alkane to its corresponding alkene, which provide improved selectivity and yield of the desired product alkene would be welcomed by industry. It is believed that the processes and catalysts of the present invention address these needs.

SUMMARY OF THE INVENTION

The present invention provides a process for producing an unsaturated carboxylic acid or an unsaturated nitrile from the corresponding $C_2$-$C_4$ alkane. The process comprises: A) contacting a $C_2$-$C_4$ alkane and oxygen with an upstream catalyst in an exothermic reaction zone, wherein the upstream catalyst is catalytically active for the exothermic conversion of the $C_2$-$C_4$ alkane to its corresponding $C_2$-$C_4$ alkene, in the presence of oxygen; and B) exothermically converting a portion of the $C_2$-$C_4$ alkane to the corresponding $C_2$-$C_4$ alkene, in the exothermic reaction zone, to produce a heated mixed product gas which comprises the corresponding $C_2$-$C_4$ alkene, unreacted $C_2$-$C_4$ alkane, and heat produced by said exothermically converting step. The process further comprises C) contacting the heated mixed product gas and a weak oxidant with a downstream catalyst in an endothermic reaction zone, wherein the downstream catalyst is catalytically active for the endothermic conversion of the unreacted $C_2$-$C_4$ alkane to the corresponding $C_2$-$C_4$ alkene, in the presence of the weak oxidant; D) endothermically converting at least a portion of the unreacted $C_2$-$C_4$ alkane to the corresponding $C_2$-$C_4$ alkene, in the endothermic reaction zone, to produce a cumulative product stream which comprises at least the corresponding $C_2$-$C_4$ alkene produced in each of the reaction zones. The cumulative product stream is then E) cooled and dried before F) separating $C_2$-$C_4$ alkene, unreacted $C_2$-$C_4$ alkane and unreacted carbon dioxide from the cooled cumulative product stream by absorption with a solvent to produce an organic-rich solvent stream comprising the separated $C_2$-$C_4$ alkene, unreacted $C_2$-$C_4$ alkane and unreacted carbon dioxide, and a stream comprising non-absorbed constituents. The $C_2$-$C_4$ alkene, unreacted $C_2$-$C_4$ alkane and unreacted carbon dioxide are separated H) from the organic-rich solvent stream to produce a recovery stream comprising recovered $C_2$-$C_4$ alkene, $C_2$-$C_4$ alkane and carbon dioxide. The recovery stream comprising the $C_2$-$C_4$ alkene is oxidized to produce an oxidation product stream comprising the corresponding unsaturated carboxylic acid or nitrile, in the presence of at least one catalyst capable of facilitating the oxidizing reaction. The oxidation product stream is separated I) to form an aqueous oxidation product stream comprising the corresponding unsaturated carboxylic acid or nitrile, and a gas stream comprising unreacted $C_2$-$C_4$ alkane and unreacted carbon dioxide. Finally, the integrated process of the present invention comprises drying the gas stream and separating the unreacted $C_2$-$C_4$ alkane and unreacted carbon dioxide therefrom; and K) recycling the separated unreacted $C_2$-$C_4$ alkane and unreacted carbon dioxide to the exothermic converting step.

In one embodiment the upstream catalyst comprises an oxidative dehydrogenation catalyst comprising at least one catalyst composition selected from the group consisting of: A) a catalyst comprising one or more noble metals selected from Pt, Pd, Rh, Ir and Ru; and B) a catalyst comprising at least one oxide of a metal selected from Li, Mo, W, V, Nb, Sb, Sn, Ga, Zr, Mg, Mn, Ni, Co, Ce and rare-earth metals.

In one embodiment the downstream catalyst comprises an endothermic dehydrogenation catalyst comprising at least one catalyst composition selected from the group consisting of: A) a catalyst comprising chromium oxide and, optionally, oxides of at least one metal selected from the group consisting of Mo, W, V, Ga, Mg, Ni, Fe, alkali elements, alkali earth elements, and rare earth elements; B) a catalyst comprising vanadium oxide and, optionally, at least one element selected from the group consisting of Li, Na, K and Mg; C) a catalyst comprising platinum and, optionally, at least one metal selected from the group consisting of sodium, potassium, cesium, rhenium and tin; and D) a catalyst comprising at least one metal selected from the group consisting of Ga, Fe, Mn and Co.

In a particular embodiment of the process of the present invention, the $C_2$-$C_4$ alkane comprises propane, the corresponding $C_2$-$C_4$ alkene comprises propene, the weak oxidant comprises carbon dioxide and the unsaturated carboxylic acid comprises acrylic acid.

In another embodiment, the oxidizing step H) is performed by a two-step vapor phase catalytic oxidation wherein a first oxidation reaction zone comprises a first oxidation catalyst capable of catalyzing the conversion of the $C_2$-$C_4$ alkene to the corresponding aldehyde, and a second oxidation reaction zone, positioned downstream of the first oxidation reaction zone and comprising a second oxidation catalyst, different from the first oxidation catalyst and capable of catalyzing the conversion of the corresponding aldehyde to the corresponding unsaturated carboxylic acids or nitriles.

In still another embodiment, the unreacted $C_2$-$C_4$ alkane and unreacted carbon dioxide are separated from a downstream process stream by using a pressure swing absorption system and recycling the unreacted $C_2$-$C_4$ alkane and unreacted carbon dioxide to the exothermic reaction zone.

BRIEF DESCRIPTION OF THE DRAWINGS

A more complete understanding of the present invention will be gained from the embodiments discussed hereinafter and with reference to the accompanying drawing, wherein.

DETAILED DESCRIPTION OF THE INVENTION

The present invention provides a process for producing unsaturated carboxylic acids from the corresponding $C_2$-$C_4$ alkanes and involves an exothermic oxidative dehydrogenation reaction which converts a $C_2$-$C_4$ alkane to its corresponding $C_2$-$C_4$ alkene and produces heat, and a downstream endothermic dehydrogenation reaction which receives the product stream and heat from the exothermic reaction and converts additional quantities of the $C_2$-$C_4$ alkane to the same corresponding $C_2$-$C_4$ alkene. The product $C_2$-$C_4$ alkene is then subjected to two stage vapor phase catalytic partial oxidation to produce the corresponding unsaturated carboxylic acids. The reactions are performed in sequence and are integrated so that the heat produced incidentally in the exothermic reaction is subsequently utilized in the endothermic dehydrogenation reaction to produce additional quantities of alkene, which is then provided directly and continuously to the partial oxidation process. Operating the exothermic and endothermic dehydrogenation reactions in the integrated manner stated above minimizes the need for additional fuel and increases the overall selectivity to, and yield of, the product alkene, which can then be provided directly to the partial oxidation reactors, thereby increasing the selectivity and yield of unsaturated carboxylic acid.

The following definitions and meanings are provided for clarity and will be used hereinafter.

The term "hydrocarbon" means a compound which comprises at least one carbon atom and at least one hydrogen atom.

As used herein, the term "$C_2$ to $C_4$ alkane" means a straight chain or branched chain alkane having from 2 to 4 carbons atoms per alkane molecule, for example, ethane, propane and butane, which are typically in the vapor phase at ordinary temperatures and pressures (e.g., at least 10° C. and 1 atmosphere). Accordingly, the term "$C_2$ to $C_4$ alkene" means a straight chain or branched chain alkene having from 2 to 4 carbons atoms per alkene molecule, for example, ethane, propene and butene.

The term "corresponding $C_2$-$C_4$ alkene" means the alkene having the same number of carbon atoms per alkene molecule as the alkane under discussion.

The term "corresponding $C_2$-$C_4$ unsaturated carboxylic acid" means the unsaturated carboxylic acid having the same number of carbon atoms per carboxylic acid molecule as the starting alkene.

Furthermore, as used herein, the term "$C_2$ to $C_4$ alkanes and alkenes" includes at least one of the aforesaid $C_2$-$C_4$ alkanes, as well as its corresponding $C_2$-$C_4$ alkene. Similarly, when used herein in conjunction with the terms "$C_2$ to $C_4$ alkane", or "$C_2$ to $C_4$ alkene", or "$C_2$ to $C_4$ alkanes and alkenes", the terminology "a mixture thereof," means a mixture that includes at least one of the aforesaid alkanes having from 2 to 4 carbons atoms per alkane molecule, and the alkene having the same number of carbons atoms per alkene molecule as the alkane under discussion, for example, without limitation, a mixture of propane and propene, or a mixture of n-butane and n-butene.

An "inert" material, sometimes also referred to as a "diluent," is any material which is substantially inert, i.e., does not participate in, is unaffected by, and/or is inactive, in the particular reaction of concern. For example, nitrogen is inert in reactions that convert alkanes to their corresponding alkenes. As a more specific example, nitrogen is inert in oxidative dehydrogenation reactions that produce propene from propane. In the context of catalysts, where a mixed metal oxide catalyst useful in oxidation reactions is supported by a zirconium-based material, the zirconium-based material is considered to be inert and, therefore, does not directly affect, and is not directly affected by, the oxidation reaction being catalyzed by the mixed metal oxide catalyst. (Rather, without being bound by theory, it is believed that some support materials, such as zirconium, directly interact with the catalyst, which in turn may affect the conversion, selectivity, etc., of the oxidation reaction.)

The term "oxygen-containing gas," as used herein, means any gas comprising from 0.01% up to 100% oxygen or oxygen-containing compounds, including for example, without limitation: air, oxygen-enriched air, nitrous oxide, nitrogen dioxide, pure oxygen, mixtures of pure oxygen or oxygen-containing compounds with at least one inert gas, such as nitrogen, and mixtures thereof. Although the oxygen containing gas may be pure oxygen gas, it is usually more economical to use an oxygen containing gas, such as air, when purity is not particularly required.

"Oxidative dehydrogenation," as used herein, means a chemical reaction in which a hydrocarbon and oxygen are reacted to result in removal of one or more hydrogen atoms from the hydrocarbon to produce oxidation products. Thus, as this term is used herein, oxidative dehydrogenation requires an oxygen-containing gas or a gaseous oxygen-containing compound to provide the required oxygen.

"Exothermic oxidative dehydrogenation," as used herein, means an oxidative dehydrogenation process which produces heat in addition to oxidation product compounds.

"Endothermic dehydrogenation," as used herein, means a chemical reaction in which one or more hydrogen atoms are removed from a hydrocarbon, and which consumes heat, and so requires heat to be supplied from a source outside the reaction.

Endpoints of ranges are considered to be definite and are recognized to incorporate within their tolerance other values within the knowledge of persons of ordinary skill in the art, including, but not limited to, those which are insignificantly different from the respective endpoint as related to this invention (in other words, endpoints are to be construed to incorporate values "about" or "close" or "near" to each respective endpoint). The range and ratio limits, recited herein, are combinable. For example, if ranges of 1-20 and 5-15 are recited for a particular parameter, it is understood that ranges of 1-5, 1-15, 5-20, or 15-20 are also contemplated and encompassed thereby.

The process of the present invention involves sequential, thermally integrated dehydrogenation reactions DH (see FIG. 1), each of which converts a particular $C_2$-$C_4$ alkane to the same corresponding $C_2$-$C_4$ alkene, as well as downstream partial oxidation reactions PO (see FIG. 1), which convert the $C_2$-$C_4$ alkene product to corresponding unsaturated carboxylic acids. Since the thermally integrated dehydrogenation processes DH produce a greater total yield of the corresponding $C_2$-$C_4$ alkene, with greater overall thermal efficiency, than either dehydrogenation reaction alone, the ultimate yield of corresponding unsaturated carboxylic acids from the subsequent partial oxidation reactions PO is also increased compared to conventional, known oxidation processes for producing unsaturated carboxylic acids from the corresponding $C_2$-$C_4$ alkenes.

The overall integrated process, as well as catalysts suitable for use therein, will first be described in general. Then a more detailed description is provided of an exemplary embodiment of the present invention, which is a combination of an exothermic oxidative dehydrogenation reaction and an endothermic dehydrogenation reaction for converting propane to propene, followed by two-stage vapor phase partial oxidation of the propene to produce unsaturated carboxylic acid (i.e., acrylic acid), will be provided in the examples.

Notwithstanding the specificity of the exemplary embodiments, it will be appreciated and understood by persons of ordinary skill that the present invention is applicable to other types of reactions and products, and is subject to modifications and alterations, as necessary and desired, according to the ordinary skill and general knowledge of persons practicing in the relevant art. For example, the process of the present invention may be easily adapted by skilled persons to dehydrogenate a variety of hydrocarbons such as isopropane, ethane and ethyl benzene.

Figure 1:
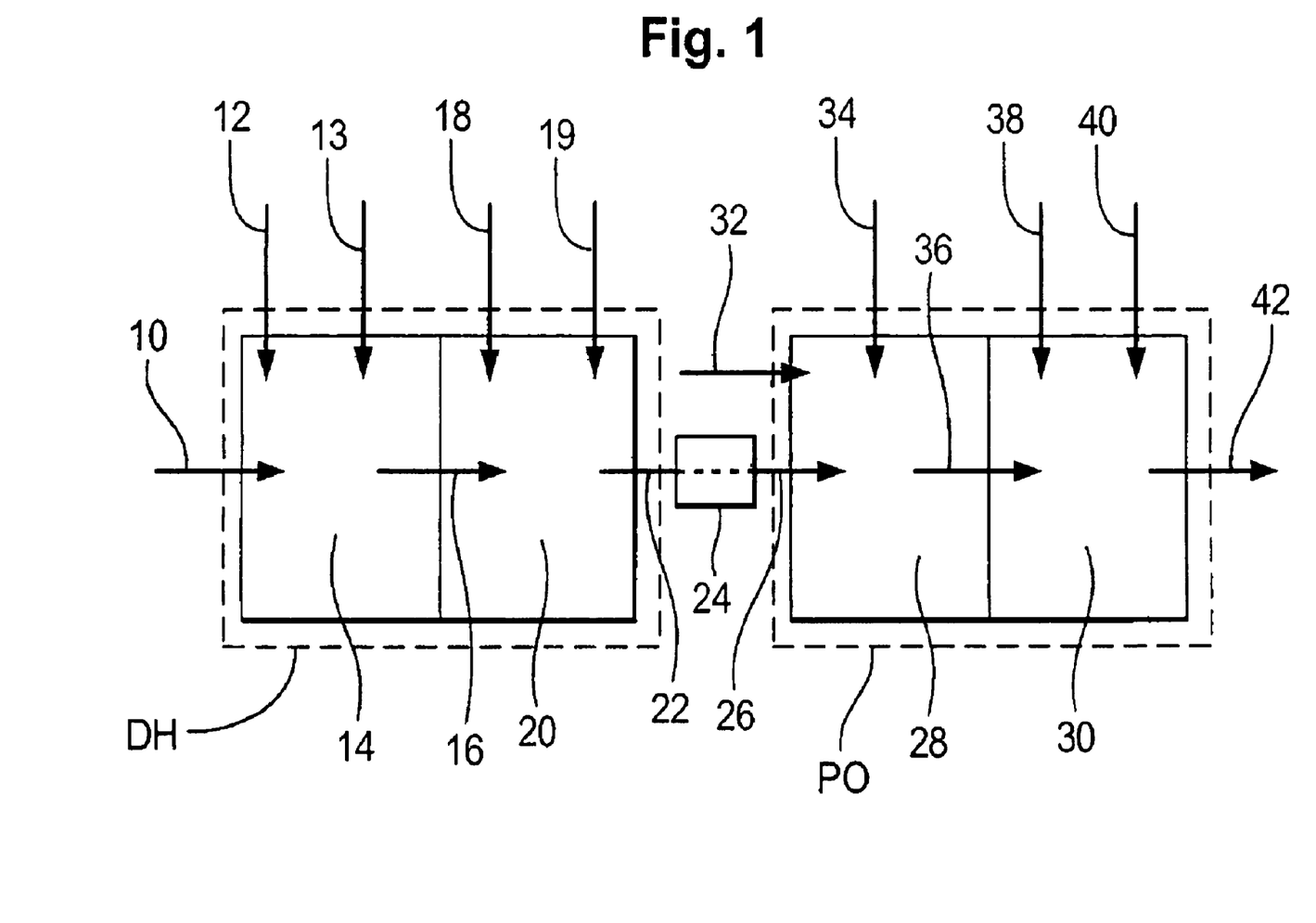
FIG. 1 is a generalized schematic representation of the process of the present invention.

Referring now to the schematic representation of the integrated process of the present invention provided in FIG. 1, generally, a $C_2$-$C_4$ alkane 10 and oxygen 12 are contacted with an upstream catalyst (not shown per se) in an exothermic reaction zone 14. The upstream catalyst is catalytically active for the exothermic conversion of the $C_2$-$C_4$ alkane to its corresponding $C_2$-$C_4$ alkene in the presence of oxygen. The oxygen 12 may be supplied in the form of an oxygen-containing gas, as is well-known by persons of ordinary skill. The $C_2$-$C_4$ alkane 10 and oxygen 12 may be supplied to the exothermic reaction zone 14 separately and simultaneously, (as shown in FIG. 1), or they may be blended together (not shown) and the resulting blended stream supplied to the exothermic reaction zone 14. One or more inert materials, or diluents 13, may also be provided to the exothermic reaction zone 14, separately or mixed with either, or both, of the $C_2$-$C_4$ alkane 10 and oxygen 12. Suitable diluents include, but are not limited to nitrogen, carbon dioxide, noble gases and steam. The total feed composition to the exothermic reaction zone 14 may be, for example, 5-50 vol % alkane, 2-30 vol % oxygen, 0-50 vol % carbon dioxide, and the remainder nitrogen, based upon the total volume of the feed materials. Another example of a suitable feed composition for the endothermic reaction zone may be, without limitation, 5-20 vol % alkane, 2-15 vol % oxygen, 10-40 vol % carbon dioxide, and the remainder nitrogen, based upon the total volume of the feed materials.

A portion of the $C_2$-$C_4$ alkane is exothermically converted in the exothermic reaction zone 14, producing a heated mixed product gas 16 comprising at least the corresponding $C_2$-$C_4$ alkene, unreacted $C_2$-$C_4$ alkane, and heat produced by the exothermic conversion of the aforesaid portion of the $C_2$-$C_4$ alkane. The heated mixed product gas 16 may further comprise compounds including, but not limited to, carbon monoxide, carbon dioxide, other carbon-containing compounds, and water.

With reference still to FIG. 1, the process of the present invention further comprises contacting the heated mixed product gas 16 and a mild oxidant, such as carbon dioxide 18, with a downstream catalyst (not shown per se) in an endothermic reaction zone 20. The downstream catalyst is catalytically active for the endothermic conversion of the unreacted $C_2$-$C_4$ alkane to the same corresponding $C_2$-$C_4$ alkene as produced in the exothermic reaction zone 14. Carbon dioxide 18 may be supplied to the endothermic reaction zone 20 in any manner known to persons of ordinary skill in the art. For example, as shown in FIG. 1, carbon dioxide 18 may be provided as a separate stream directly to the endothermic reaction zone 20, simultaneously with the heated mixed product gas 16. Other options, which are not shown here, include, but are not limited to: blending the carbon dioxide 18 with the heated mixed product gas 16 before entry into the endothermic reaction zone 20, or blending the carbon dioxide 18 with one or more of the feed streams to the exothermic reaction zone 14 (i.e., with one or both of the $C_2$-$C_4$ alkane 10 and oxygen 12). One or more inert materials, or diluents 19, may also be provided to the endothermic reaction zone 20, separately or mixed with either, or both, of the heated mixed product gas 16 and carbon dioxide 18. Suitable diluents include, but are not limited to nitrogen, noble gases and steam. The feed composition to the endothermic reaction zone 20 may be, for example, 5-50 vol % alkane, 0-5 vol % oxygen, 10-80 vol % carbon dioxide, and the remainder nitrogen, based upon the total volume of the feed materials. Another example of a suitable feed composition for the endothermic reaction zone may be, without limitation, 5-20 vol % alkane, 0-2 vol % oxygen, 20-60 vol % carbon dioxide, and the remainder nitrogen, based upon the total volume of the feed materials.

At least a portion of the unreacted $C_2$-$C_4$ alkane is endothermically converted, in the endothermic reaction zone 20, to produce a cumulative product stream 22 which comprises at least the corresponding $C_2$-$C_4$ alkene formed in each of the exothermic and endothermic reaction zones 14, 20. The cumulative product stream 22 may also comprise one or more of the following compounds: unreacted $C_2$-$C_4$ alkane, unreacted oxygen, unreacted carbon dioxide, as well as other compounds including, but not limited to, carbon monoxide, water vapor, and hydrogen. The cumulative product stream 22 may be further processed to purify the desired corresponding $C_2$-$C_4$ alkene product by separating at least a portion of unreacted reactants and other compounds from the cumulative product stream 22. The separated unreacted reactants may be recycled back to one or both of the dehydrogenation reaction zones, or otherwise used or disposed of. For example, the cumulative product stream 22 may be subjected to one or more interim treatments 24, such as, without limitation, drying, compression, and stripping, to produce an oxidation feed stream 22a comprising at least unreacted propane, propene and carbon dioxide, which may then fed to partial oxidation reaction zones 26, 28, as described in further detail hereinafter.

Determination of the quantities and how to supply the reactant materials ($C_2$-$C_4$ alkane, oxygen, carbon dioxide, etc.) to each of the exothermic and endothermic reaction zones is well within the ability of persons of ordinary skill in the art, based upon the knowledge generally available as well as the particular reactions, the desired products, and the catalysts selected for use in the reaction zones. For example, where carbon dioxide is expected to interfere with the performance of the selected upstream catalyst, then the carbon dioxide should not be blended with the initial reactant materials ($C_2$-$C_4$ alkane and oxygen) supplied to the exothermic reaction zone, but rather, the carbon dioxide should be blended with the heated mixed product gas, or supplied directly to the endothermic reaction zone. Conversely, where it is not possible to supply the carbon dioxide to the endothermic reaction zone, either directly or blended with the heated mixed product gas, then an upstream catalyst should be selected which can tolerate the presence of carbon dioxide. Where the performance of the downstream catalyst would be adversely affected by the presence of oxygen, the operating conditions in the oxidative reaction zone (e.g., temperature and bed size) may be adjusted for total consumption of the oxygen and, consequently, the heated mixed product gas provided to the endothermic reaction zone will be suitably oxygen free.

Catalysts suitable for use in the process of the present invention are not particularly limited and are generally known in the art. Suitable upstream and downstream catalysts are simply those which are catalytically active for the particular reaction that is to occur in each of the exothermic and endothermic reaction zones, respectively.

The upstream and downstream catalysts may be prepared by any suitable method known in the art, now or in the future. For example, the catalyst can be prepared by incipient wetness impregnation, chemical vapor deposition, hydrothermal synthesis, salt melt method, co-precipitation, and other methods. As will be discussed in further detail hereinafter, catalysts which are active for exothermic or endothermic conversion of $C_2$-$C_4$ alkanes to produce the corresponding $C_2$-$C_4$ alkenes typically comprise one or more metals and/or metal oxides. In addition, either or both of the upstream and downstream catalysts may be promoted, for example, with suitable metals or metal oxides.

Furthermore, either or both of the upstream and downstream catalysts may further comprise support material. The catalyst materials may be applied to the support by any method known in the art and at any time including, but not limited to, during preparation of the catalyst material, before or after calcination, and, even before or after addition of a promoter. Typical and suitable support materials include, but are not limited to: magnesium oxide, zirconia, stabilized zirconia, zirconia stabilized alumina, yttrium stabilized zirconia, calcium stabilized zirconia, alumina, titania, silica, magnesia, nitrides, silicon carbide, cordierite, cordierite-alpha alumina, alumina-silica magnesia, zircon silicate, magnesium silicates, calcium oxide, silica-alumina, alumina-zirconia, alumina-ceria, and combinations thereof. Additionally, suitable catalyst supports may comprise rare earth metal oxides, mixed metal oxides, mesoporous materials, refractory materials, and combinations thereof. The support may be modified, stabilized, or pretreated in order to achieve the proper structural stability desired for sustaining the operating conditions under which the catalysts will be used.

The support can be in the shape of wire gauzes, monoliths, particles, honeycombs, rings, and others. Where the support is in the form of particles, the shape of the particles is not particularly limited and may include granules, beads, pills, pellets, cylinders, trilobes, spheres, irregular shapes, etc.

Monoliths typically comprise any unitary piece of material of continuous manufacture, such as, for example, pieces of metal or metal oxide, foam materials, or honeycomb structures. It is known in the art that, if desired, a reaction zone may comprise two or more such catalyst monoliths stacked upon one another. For example, the catalyst can be structured as, or supported on, a refractory oxide "honeycomb" straight channel extrudate or monolith, made of cordierite or mullite, or other configuration having longitudinal channels or passageways permitting high space velocities with a minimal pressure drop.

Furthermore, the catalyst material may be deposited as washcoats on the monolithic support by methods known to people skilled in the art. Additionally, catalyst material may be combined with the monolithic support by depositing the support material as washcoats and, successively, impregnating the support material washcoats with the active catalyst material, such as, without limitation, vanadium oxide or platinum, followed by calcination of the combined support and catalyst materials.

Monolithic supports may comprise stabilized zirconia (PSZ) foam (stabilized with Mg, Ca or Y), or foams of α-alumina, cordierite, ceramics, titania, mullite, zirconium-stabilized α-alumina, or mixtures thereof. Monolithic supports may also be fabricated from metals and their alloys, such as, for example, aluminum, steel, fecralloy, hastalloy, and others known to persons skilled in the art. Additionally, other refractory foam and non-foam monoliths may serve as satisfactory supports. The promoter metal precursor and any base metal precursor, with or without a ceramic oxide support forming component, may be extruded to prepare a three-dimensional form or structure such as a honeycomb, foam or other suitable tortuous-path or straight-path structure.

As is apparent to persons of ordinary skill in the art, the exothermic and endothermic reaction zones 14, 20 may be contained in a single reactor (not shown in FIG. 1, but see FIGS. 2 and 3), which may be any suitable reactor known in the art including, but not limited to, a batch reactor, a stirred tank reactor, a continuous stirred tank reactor (CSTRs), a tubular reactor, a shell-and-tube heat exchanger reactor, a multiple-pass reactor, a reactor having microchannels, a short contact time reactor, a catalytic fixed bed reactor, and a reactor having a combination of the foregoing features. Each reaction zone 14, 20 may, instead, be disposed within separate reactors (not shown), and various combinations of reactors and reaction zones may be arranged. Each reaction zone 14, 20 may or may not include sub-zones (also not shown), which differ by operating temperature, or catalyst composition, or catalyst concentration, or in other ways which are known to persons of ordinary skill. Furthermore, the upstream and downstream catalysts may be configured in their respective reaction zones in any suitable arrangement including, but not limited to, a fixed bed, a fluidized bed, and a spouted bed. All such configurations are well known in the art.

As discussed in further detail hereinafter in connection with an exemplary embodiment, it is within the ability of persons of ordinary skill in the relevant art to select appropriate operating conditions for each of the exothermic and endothermic reaction zones, depending on the particular products desired and the reactions and catalysts selected to produce the desired product.

In an exemplary embodiment, the upstream catalyst may be an oxidative dehydrogenation catalyst (ODH catalyst) which catalyzes the exothermic catalytic oxidative dehydrogenation of a $C_2$-$C_4$ alkane with oxygen, to produce the corresponding $C_2$-$C_4$ alkene and heat. Furthermore, the upstream catalyst may, for example, be contained in a fixed bed, tubular reactor.

Persons of ordinary skill will be familiar with various ODH catalysts that may be successfully used in the exothermic reaction zone, in accordance with process of the present invention. Suitable categories of ODH catalysts include, but are not limited to: catalysts comprising one or more noble metals selected from Pt, Pd, Rh, Ir and Ru; and catalysts comprising at least one oxide of a metal selected from Li, Mo, W, V, Nb, Sb, Sn, Ga, Zr, Mg, Mn, Ni, Co, Ce and rare earth metals. For example, mixed metal oxide catalysts having, as essential elements, Mo—Sb—W or Cr—Sb—W, and at least one metal selected from the group consisting of V, Nb, K, Mg, Sn, Fe, Co and Ni; as well as vanadium-aluminum-based mixed metal oxide catalysts, with or without one or more additional metal oxides of Nb, Cr, Zn, Fe, Mo, Mg and rare earth elements; and, furthermore, vanadium-based catalysts promoted with one or more of La, Ce, Pr, Sm and Er, have all been shown to catalyze the exothermic oxidative dehydrogenation of propane to form propene. In an exemplary embodiment, the ODH catalyst comprises, as essential materials, vanadium oxide and at least one oxide of a metal selected from the group consisting of: niobium, magnesium, molybdenum and rare earth elements As already mentioned, the ODH catalysts may be supported by materials such as alumina, platinum, silica, other metal oxides, microporous materials, mesoporous materials, and refractory materials. For example, a vanadium-niobium-oxide catalyst may be combined and supported on a silicon oxide support material and advantageously used in the exothermic reaction zone of the process of the present invention.

Applicants have surprisingly found that high activity ODH catalysts, such as vanadium-oxide-based catalysts supported on certain materials such as alumina, zirconia, or titania (as opposed to, for instance, silica), will catalyze the exothermic ODH conversion of propane to propene better if the supported catalyst is loaded onto a monolithic carrier, rather than if used alone in particulate (powder) form. For example, a silica-supported vanadium-based ODH catalyst was found to provide similar performance for ODH of propane, regardless of whether deposited on a cordierite monolith as washcoats, or simply used in powder form (having average particulate size of 300-500 microns). However, surprisingly, an alumina-supported vanadium-based catalyst composition loaded onto a cordierite monolith carrier as washcoats performed better for ODH of propane, than when used in powder form (also having average particulate size of 300-500 microns). Furthermore, similar performance improvements are expected even when the monolithic carrier is formed from materials other than cordierite, such as, for example, metal or ceramic, in the form of any unitary body including, but not limited to a monolith, a honeycomb, a plate, foam, heat exchanger components, reactor chamber walls, etc.

Suitable operating conditions for oxidative dehydrogenation of a $C_2$-$C_4$ alkane in the exothermic reaction zone are generally known in the art and determinable by persons of ordinary skill. For example, the $C_2$-$C_4$ alkane, oxygen and, optionally, a diluent, are typically supplied to the exothermic reaction zone, separately or in various combinations with one another, at a total gas hourly space velocity (GHSV) of between about 1,000 $hr^{-1}$ to 1,000,000 $hr^{-1}$, for example, between about 5,000 $hr^{-1}$ and 200,000 $hr^{-1}$, or even 5,000 $hr^{-1}$ to 10,000 $hr^{-1}$. The reaction pressure is typically in the range of from 0.1 to about 10 atmospheres (atm), for example, from 0.8 to 5.0 atm; and the reaction temperature is typically maintained between 400° C. and 1,100° C., for example, between 450° C. and 650° C. Contact time between the reactants and catalyst is typically in the range of from 10 milliseconds (ms) (360,000 $h^{-1}$) to 4 seconds (900 $h^{-1}$). The molecular ratio of $C_2$-$C_4$ alkane to oxygen supplied to the exothermic reaction zone may, for example, be in a range of from 1:1 to 10:1, such as between 1:1 and 5:1.

In this exemplary embodiment, when the selected upstream catalyst is an ODH catalyst, the downstream catalyst may be an endothermic dehydrogenation catalyst which catalyzes the endothermic dehydrogenation of the same $C_2$-$C_4$ alkane, in the presence of a mild oxidant, to the same corresponding $C_2$-$C_4$ alkene as the ODH catalyst in the exothermic reaction zone. For example, if the upstream catalyst is an oxidative dehydrogenation catalyst which converts propane to propene, then the downstream catalyst may be an endothermic dehydrogenation catalyst which also converts propane to propene. The mild oxidant may be, for example, without limitation, carbon dioxide, steam, or a combination thereof. As discussed hereinabove, many such endothermic dehydrogenation catalysts are known and would be suitable for use the endothermic reaction zone in accordance with process of the present invention.

Persons of ordinary skill will be familiar with various endothermic dehydrogenation catalysts that may be successfully used in the endothermic reaction zone, in accordance with process of the present invention. Suitable categories of endothermic dehydrogenation catalysts include, but are not limited to: chromium oxide-based catalysts, which may also comprise oxides of at least one metal selected from the group consisting of Mo, W, V, Ga, Mg, Ni, Fe, alkali elements, alkali earth elements, and rare earth elements; as well as vanadium oxide-based catalysts, which may be promoted with Li, Na, K or Mg; platinum-based catalysts which may also comprise at least one metal selected from the group consisting of sodium, potassium, cesium, rhenium and tin; and a catalyst comprising at least one metal selected from the group consisting of Ga, Fe, Mn and Co.

As will be easily recognized by skilled persons, there are many catalyst compositions suitable for use in the endothermic reaction zone in accordance with the present invention. For example, the endothermic dehydrogenation catalyst may comprise a vanadium-chromium-oxide, and, optionally, at least one oxide of a metal selected from the group consisting of: copper, silver, and gold. The vanadium-chromium-oxide catalyst may also comprise oxides of one or more metals selected from the group consisting of: Cu, Ag, Au, K, Cs, Pt, Rh, and additional metal oxides. Furthermore, the vanadium-chromium-oxide catalysts may be modified with one or more reagents selected from the group consisting of: phosphate and sulfate.

As already mentioned, the endothermic dehydrogenation catalysts may be combined and supported on materials such as alumina, platinum, silica, zirconia, zeolites, other metal oxides, microporous materials, mesoporous materials, and refractory materials. For example, silicon oxide material or mesoporous material, such as MCM-41, may be used to support a vanadium oxide-based catalyst, such as V/Cr/Si/O, V/Cr/Ag/Si/O, V/Cr/Ag/Cs/Silo, and others. Additionally, other examples include, without limitation: a V/Cr/Mn/W/O catalyst supported on alumina, platinum oxide-based catalysts supported on a microporous zeolite material such as ZSM-5, and a V/Cr/AgO catalyst supported on gallium oxide material (e.g., β-$Ga_2O_3$). As will be easily recognized by skilled persons, there are many combinations of catalyst compositions and support materials that will be suitable for use in the endothermic reaction zone in accordance with the present invention.

Suitable operating conditions for endothermic dehydrogenation of a $C_2$-$C_4$ alkane are generally known by persons of ordinary skill and are applicable to operation of the endothermic reaction zone. For example, carbon dioxide, the heated mixed product gas comprising unreacted $C_2$-$C_4$ alkane and, optionally, a diluent, may be supplied to the endothermic reaction zone, separately or mixed, at a total gas hourly space velocity (GHSV) of about 500 $hr^{-1}$ to 100,000 $hr^{-1}$. The reaction pressure is typically in the range of from 0.1 to about 10 atm, for example, from 0.8 to 5.0 atm, and the reaction temperature is typically maintained between 300° C. and 900° C., for example, between 450° C. and 700° C. Contact time between the reactants and catalyst is typically in the range of from 36 ms (100,000 h$^{-1}$) to 7.2 seconds (500 h$^{-1}$), such as, for example, from 200 ms to 5 seconds. The molecular ratio of unreacted $C_2$-$C_4$ alkane to mild oxidant, such as carbon dioxide, supplied to the exothermic reaction zone may, for example, be in a range of from 1:0.1 to 1:10, or even between 1:1 and 1:5. It is noted that short contact time (SCT) operating conditions have been used, as an alternative to traditional steam cracking and non-oxidative dehydrogenation processes, to perform oxidative dehydrogenation of $C_2$-$C_4$ alkenes, wherein the contact time of the reactants with the oxidative dehydrogenation catalyst is typically in the range of 1 to 650 ms, under temperatures of between 200° C. and 1100° C., and pressures of from 0.3 atm to 40 atm.

After further processing of the dehydrogenation effluent stream 22, the resulting oxidation feed stream comprises propene, unreacted propane, and carbon dioxide. With reference back to FIG. 1, the oxidation feed stream 26 is fed, sequentially, to the partial oxidation reaction zones PO, 28, 30. In particular, as shown schematically in FIG. 1, the oxidation feed stream 26, along with an oxygen-containing gas 32 and, optionally, steam 34, is provided to the first 28 of two oxidation reaction zones 28, 30. Addition of oxygen-containing gas to the starting materials provides molecular oxygen to the reaction system. It is usually most economical to use an oxygen-containing gas such as air, since purity is not particularly required.

Any type of reactors that are suitable for performing the desired vapor phase oxidation reactions may be used to contain, or hold, the oxidation reaction zones 28, 30. Shell-and-tube reactors, for example and without limitation, are suitable for use in this regard.

Suitable diluting gases may also be provided to the first oxidation reaction zone 28, including, but not limited to, one or more of: carbon monoxide, carbon dioxide, or mixtures thereof, an inert gas, such as nitrogen, argon, helium, or mixtures thereof. A suitable molar ratio of the starting materials for the total feed materials to the first oxidation reaction zone 28, ($C_2$-$C_4$ alkane, $C_2$-$C_4$ alkene, or a mixture thereof): (oxygen):($H_2O$):(diluting gas), would be, for example, (1): (0.1 to 10):(0 to 20):(0.2 to 70), for example, including but not limited to, (1):(1 to 5.0):(0 to 10):(5 to 40). Where it is desired to produce unsaturated carboxylic acids, it is beneficial to include steam 34 among the starting materials, as shown in FIG. 1 and mentioned hereinabove. The steam to be employed may be present in the form of steam gas in the reaction system, and the manner of its introduction is not particularly limited.

When steam is supplied together with the mixture of $C_2$-$C_4$ alkanes and alkenes, as starting material gas, the selectivity for an unsaturated carboxylic acid is distinctly improved, and the unsaturated carboxylic acid can be obtained in good yield. However, the conventional technique utilizes a diluting gas, as described above, for the purpose of diluting the starting material. Such a diluting gas is used to adjust the space velocity, the oxygen partial pressure and the steam partial pressure, as will be readily understood by persons having ordinary skill in the art.

If it is desired to produce unsaturated nitriles from the corresponding $C_2$-$C_4$ alkanes, ammonia (not shown) must also be provided to the first oxidation reaction zone 28. In such cases, the ammonia may be provided simultaneously, but separately from the oxidation feed stream 26, or any of the other feed streams 32, 34. Alternatively, the ammonia may be combined with any one or more of the other feed streams 26, 32, 34 to the first oxidation reaction zone 28.

With reference now to the oxidation reaction zones 28, 30, one or more oxidation catalysts (not shown, per se) are contained within each oxidation reaction zone 28, 30. The oxidation catalysts are capable of facilitating the desired vapor phase oxidation reaction, in this case, partial oxidation of a $C_2$-$C_4$ alkene (e.g., propene) to the corresponding unsaturated carboxylic acid (e.g., acrylic acid). The oxidation catalysts may be of different configuration, including but not limited to fixed-bed, moving-bed and fluidized-bed. In addition, any suitable catalyst may be used and would be selected based upon the particular $C_2$-$C_4$ alkane, $C_2$-$C_4$ alkene, or mixture thereof, and the desired oxidation products. As is well known in the art, the catalysts may be used alone, or they may also be used together with a carrier, or support, such as, without limitation, silica, alumina, titania, aluminosilicate or diatomaceous earth. Further, depending upon the scale or system of the reaction, they may be molded into a proper shape and/or particle size. The particular shape or geometry of the catalysts are not particularly limited in connection with the present invention.

The selection of the catalysts, their shape, size and packing method, are well within the ability of persons having ordinary skill in the art. In general, any catalysts that are capable of catalyzing the two-step vapor phase catalytic oxidation of a reactive hydrocarbon to an unsaturated aldehyde or acid are suitable for use in connection with the present invention. For example, one embodiment of the multiple catalyst system of the present invention is capable of catalyzing propene to acrylic acid. Although the following discussion will describe the multiple catalyst system as applied to the production of acrylic acid from propene by two-step vapor phase catalytic oxidation, it will be understood, as previously described, that the present invention is not limited to such application and is suitable for use in the production of other unsaturated aldehydes and acids from other types of reactive hydrocarbons.

Catalysts capable of oxidizing an alkene to the corresponding aldehyde are hereinafter referred to as "first oxidation catalysts" and are suitable for use with the present invention, as will be discussed in further detail hereinafter. In addition, catalysts capable of oxidizing the aforesaid aldehyde to the corresponding unsaturated carboxylic acid "second oxidation catalysts". Either the first oxidation catalysts, or the second oxidation catalysts, or both, are typically, but need not be, mixed metal oxide compositions.

For example, the first oxidation reaction zone 28 may contain a first oxidation catalyst and the second oxidation reaction zone 30 may contain a second oxidation catalyst. Other embodiments are possible wherein the multiple catalyst system comprises more than one type of first oxidation catalyst and a second oxidation catalyst, or alternatively, a first oxidation catalyst and more than one type of second oxidation catalyst. Furthermore, the catalysts contained in the first and second oxidation reaction zones 28, 30 may comprise more than one type of first oxidation catalyst and more than one type of second oxidation catalyst. The foregoing variations, and others, will be readily apparent to persons of ordinary skill in the art based upon the following description.

In particular, a first oxidation catalyst suitable for use in connection with the present invention comprises at least one atom of a group VIB element, at least one atom of a group VA element, and at least two group VII atoms and is capable of catalyzing the production of an aldehyde, such as acrolein. For example, the first oxidation catalyst may contain more than one atom of the same group VIII element (e.g., group VIII atoms include Fe, Co, Ni, Ru, Rh, Pd, Os, Ir, Pt). In another embodiment, the R1 catalyst comprises two group VIII atoms which are different elements. In a further embodiment, the first oxidation catalyst comprises at least Fe, Co or Ni. Yet another embodiment of first oxidation catalyst includes at least two different atoms selected from Fe, Co or Ni and compounds which are mixture thereof (e.g., FeCo, FeNi, CoFe, CoNi).

Commonly, the first oxidation catalyst comprises at least one atom of a group VIB element (e.g., Cr, Mo, W, or Unh), for example, at least Mo. In one embodiment, the first oxidation catalyst comprises at least one atom of a group VA element (e.g., N, P, As, Sb or Bi), and in another embodiment, the catalyst comprises Mo, Bi, Fe and at least one atom of Ni or Co.

For example, suitable catalysts for the oxidation of propene to acrolein are described in, for instance, U.S. Pat. Nos. 4,025, 565; 5,821,390; and 5,929,275.

A second oxidation catalyst suitable for use in connection with the present invention may comprise at least one atom of a group VIB element (e.g., Cr, Mo, W, or Unh), at least one atom of a group VB element (e.g., V, Nb, Ta, or Unp), at least one atom of a group IB element (e.g., Cu, Ag, or Au), and a group VA element (e.g., N, P, As, Sb or Bi). For example, the second oxidation catalyst may comprise one or more atoms of elements from groups including: IA (alkali metal element, e.g., H, Li, Na, K, Rb, Cs, or Fr); IIA (alkali earth metal element, e.g., Be, Mg, Ca, Sr, Ba, or Ra); IIIB which also encompasses elements of the lanthanide series and the actinide series (e.g., Sc, Y, La, Ac, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, or Lr); IVB (e.g., Ti, Zr, Hf, or Unq); VB (e.g., V, Nb, Ta, or Unp); VIIB (e.g., Mn, Tc, Re, or Uns); VIII (e.g., Fe, Co, Ni, Ru, Rh, Pd, Os, Ir, Pt); IIB (e.g., Zn, Cd, or Hg); IIIA (e.g., B, Al, Ga, In or Tl); IVA (e.g., C, Si, Ge, Sn, or Pb); VA (e.g., N, P, As, Sb, or Bi); or VIA (e.g., O, S, Se, Te, or Po).

In one embodiment, the second oxidation catalyst comprises Mo, V, Cu, W and Sb. Another embodiment, the second oxidation catalyst comprises antimony present in an amount less than about 5 wt % with a concentration of less than 3% typical and less than 1% in another embodiment. In still another embodiment, the second oxidation catalyst comprises $MoO_2$ and $MoO_3$ either individually (i.e., $MoO_2$ without $MoO_3$; or $MoO_3$ without $MoO_2$) or in combination (i.e., $MoO_2$ and $MoO_3$).

Suitable catalysts for the oxidation of acrolein to acrylic acid, for example, without limitation, are described in U.S. Pat. Nos. 3,775,474; 3,893,951; 3,954,855; 4,075,127; 4,146, 732; 4,259,211; 4,339,355; 5,177,260; and 5,739,391.

With reference still to FIG. 1, In the first oxidation reaction zone 28, the oxidation feed materials 26, 32, 34 come into contact with the first oxidation catalyst therein and react with one another to form desired oxidation products, as well as various side products and by-products, according to the particular types of $C_2$-$C_4$ alkanes and alkenes used. When the oxidation feed stream 26 comprising $C_2$-$C_4$ alkene contacts the one or more catalysts contained in the first oxidation reaction zone, an intermediate oxidation effluent stream 36 is formed, which comprises at least the corresponding aldehyde, along with unreacted alkane, alkene, carbon dioxide and oxygen. For example, without limitation, where the $C_2$-$C_4$ alkene in the oxidation feed stream 26 comprises propene, the corresponding aldehyde in the effluent stream 36 will comprise acrolein.

As shown in FIG. 1, the intermediate oxidation effluent stream 36 is fed into the second oxidation reaction zone 30, along with additional oxygen-containing gas, such as air 38, and, optionally, additional steam 40. More particularly, the additional oxygen-containing gas 38 may be first combined with the intermediate oxidation effluent stream 36 and then fed together, as a combined stream (not shown) to the second oxidation reaction zone 30. Alternatively, the additional oxygen-containing gas 38 may be fed to the second oxidation reaction zone 30 as a separate feed stream (see FIG. 1).

In the second oxidation reaction zone 30, the corresponding aldehyde and oxygen come into contact with a second oxidation catalyst situated in the second oxidation reaction 30 and react with one another to form the desired oxidation products, as well as various side products and by-products, according to the particular types of alkanes and alkenes used. A final oxidation effluent stream 42 (see FIG. 1) exits the second oxidation reaction zone 30 and typically contains, but is not limited to, one or more oxidation products (e.g., unsaturated carboxylic acid), unreacted oxygen, and unreacted $C_3$ to $C_5$ alkane or alkene, or mixture thereof, as well as reaction by-products which may include, but are not limited to, acetic acid and carbon dioxide and, possibly, unreacted water and unreacted ammonia, depending upon the starting materials used. The final oxidation effluent 42 may be fed to additional processing apparatus (not shown) to undergo separation and purification processes, as is well-known to persons having ordinary skill in the art, to recover the one or more oxidation products.

For example, as will be described in greater detail below in connection with the Examples, the final oxidation effluent stream 42 may be subjected to quenching with water in an absorber, followed by one or more separations steps to remove impurities and concentrate the acrylic acid product. Furthermore, in one embodiment, the gas from the absorber may be dried, such as in a molecular sieve dryer, and then fed to a pressure swing adsorption system to recover unreacted propane and carbon dioxide for recycle back to the dehydrogenation reaction zones. In another embodiment, pressure swing adsorption is omitted and the dried gas from the absorber is simply recycled back to the first dehydrogenation reaction zone (oxidative dehydrogenation), with the recycle amount and composition being such that separation of unreacted propane and carbon dioxide is unnecessary.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

EXAMPLES

Example 1

Figure 2:
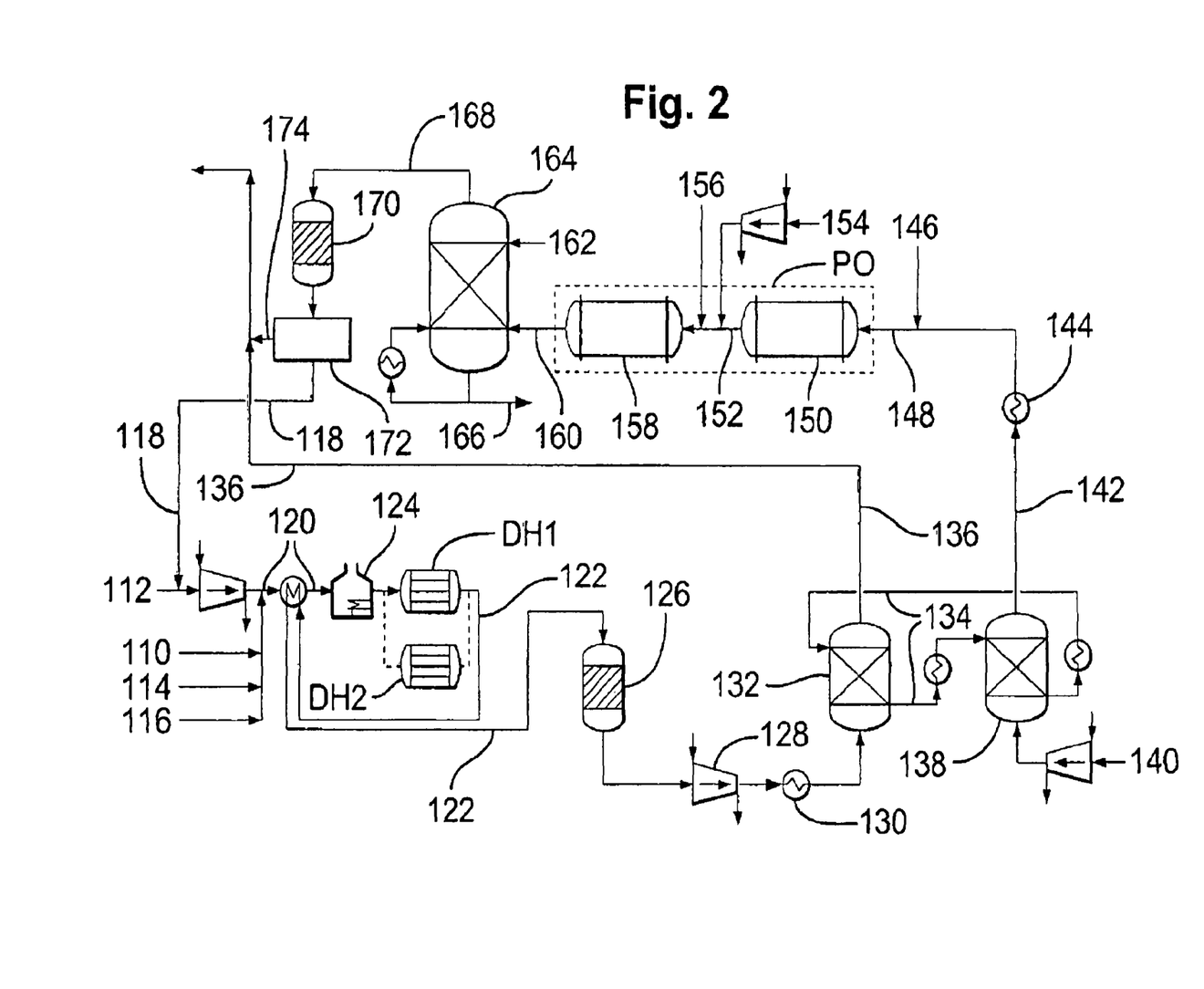
FIG. 2 is a schematic representation of a first particular example of the process of the present invention.

The following description refers to the schematic representation of process equipment shown in FIG. 2. Two dehydrogenation reactors (DH1, DH2), each comprising two oxidation reaction zones (not shown per se, but see FIG. 1 and accompanying description above), are loaded with suitable catalysts (also not shown per se, but see FIG. 1 and accompanying description above). One reactor at a time is in operation and is used to convert the propane to propene using thermally integrated dehydrogenation processes. When one reactor is not in use, i.e., "off-line," it undergoes catalyst regeneration. The dehydrogenation reactors (DH1, DH2) are automatically cycled on-line and off-line by a process control system (not shown).

The starting materials fed to the dehydrogenation reaction zones are: propane (110) at 12595 kg/hr, air (112) at 180 m³/min (STP), carbon dioxide (114) at 5317 kg/hr, and nitrogen (116) at 9348 kg/hr, and 65788 kg/hr recycle gas (118) comprising propane and carbon dioxide, each of the propane, air and recycle streams (110, 112, 118) having the compositions listed in the following Table 1:

TABLE 1

Feed Composition to Dehydrogenation Reaction Zones

| Component | % (by volume) | | |
|---|---|---|---|
| | Propane | Air | Recycle |
| Propane | 100 | | 35 |
| Nitrogen | | 79 | |
| Oxygen | | 21 | |
| Carbon Dioxide | | | 65 |

The air (112) and recycle gas (118) are combined and compressed to 2.6 bar and combined with the propane (110), $CO_2$ (114) and oxygen. The combined propane feed stream (120) is heated by exchange with the oxidative dehydrogenation reactor effluent (122) to 525° C. and then in a feed heater (124) to the reaction temperature, 625° C.

For each dehydrogenation reactor, a first zone (not shown per se) is loaded with a catalyst containing 4% $V_2O_5$-6% $Nb_2O_5$ supported on Davisil 646 for exothermic oxidative dehydrogenation of propane (alkane) to form the corresponding alkene (propene), and a second zone (not shown per se) is loaded with a catalyst containing 10% $Cr_2O_3$ supported on Merck 10181 for dehydrogenation of additional quantities of propane in the presence of a weak oxidant (the carbon dioxide), to produce more propene. Contact time in the first zone is 0.48 sec*ml/g, and the contact time in the second zone is 0.50 sec*ml/g. To obtain a heat neutral balance between the first and second dehydrogenation zones and, thus, thermally integrated dehydrogenation reaction zones, the oxygen concentration in the feed can be adjusted, plus the reactor is designed such that the heat from the first zone exothermic reaction is used provide heat to the second zone endothermic reaction. The composition of the effluent gas (122) from the dehydrogenation reaction zones is provided in the following Table 2:

TABLE 2

Product Stream Composition from Dehydrogenation Reaction Zones

| Component | % (by volume) |
|---|---|
| Carbon Dioxide | 33 |
| Carbon Monoxide | 5 |
| Ethylene | 1 |
| Hydrogen | 4 |
| Methane | 1 |
| Nitrogen | 24 |
| Propane | 17 |
| Propene | 8 |
| Water | 7 |

The cooled effluent gas (122) from the dehydrogenation reaction zones is dried in a molecular sieve dryer (126), compressed (128), and cooled (130) to 10 bar and −37° C. Propane, propene, and $CO_2$ from the effluent gas are absorbed (132) in a solvent, hexane (134). The non-absorbed constituent species (136) can either be incinerated or used as a fuel source. The organic-rich solvent is regenerated in a second column (138) by stripping the propane, propene, and $CO_2$ from the solvent with air (140) at 205 m³/min (STP). The hexane solvent (134) from the regeneration column is recycled back to the absorber (132). The recovered propane, propene, and $CO_2$ (142) are heated (144) together to 225° C. and combined with oxygen at 8936 kg/hr and steam at 3362 kg/hr (146). The first propene oxidation reactor feed stream (148) is fed to the first (150) of two partial oxidation reaction zones (PO), at a rate of 107602 kg/hr, and has the composition listed in the following Table 3:

TABLE 3

Feed Stream Composition to Partial Oxidation Reaction Zones

| Component | % (by volume) |
|---|---|
| Carbon Dioxide | 36.8 |
| Nitrogen | 15.1 |
| Oxygen | 13.9 |
| Propane | 18.9 |
| Propene | 8.7 |
| Water | 6.6 |

Propene is converted to acrolein in the first partial oxidation reaction zone (150), in the presence of a mixed metal oxide catalyst containing Mo—W—Bi—Fe—Co—Cs—Si (not shown per se). The acrolein product stream (152) from the first partial oxidation reaction zone (150) is combined with air (154) at 167 m³/min (STP) and a stream (156) 115 kg/hr, and fed to a second partial oxidation reaction zone (158), wherein the acrolein is converted to acrylic acid, in the presence of a mixed metal oxide catalyst containing as essential compounds Mo—V—W—Cu—Sb—Ti (not shown per se). The composition of the gaseous effluent stream (160) from the second partial oxidation reaction zone (158) is as follows:

TABLE 4

Effluent Stream Composition from Partial Oxidation Reaction Zones

| Component | % (by volume) |
|---|---|
| Acetaldehyde | 0.03 |
| Acetic Acid | 0.1 |
| Acrylic Acid | 6.6 |
| Acrolein | 0.03 |
| Carbon Dioxide | 33.5 |
| Nitrogen | 24.4 |
| Oxygen | 3.3 |
| Propane | 16.7 |
| Propene | 0.2 |
| Water | 15.2 |

The effluent (160) from the partial oxidation reaction zones (PO) is quenched with water (162) in an absorber (164). The aqueous, crude acrylic acid (166) is conducted to separations apparatus (not shown) to concentrate the acrylic acid and remove impurities. The gas (168) from the absorber (164) is dried in a molecular sieve dryer (170) and fed to a pressure swing adsorption system (172) to separate and recover unreacted propane and $CO_2$. In order to meet feed concentration requirements for the ODH reactor (the first dehydrogenation reaction zone), propane and $CO_2$ need to be separated and recovered from the gas from the absorber. Without such recovery, a significant portion of the gas from the absorber could not be used for recycle and would need to be discarded. The pressure swing adsorption system (172) is assumed to recover 99% of the unreacted propane and 90% of the $CO_2$. The recovered propane and $CO_2$ (118) are recycled to the dehydrogenation reactors (DH1, DH2). The non-recycled material (174) can be combined with the gas (136) from the propane/propene absorber (132), incinerated, or used as a fuel source.

Example 2

Figure 3:
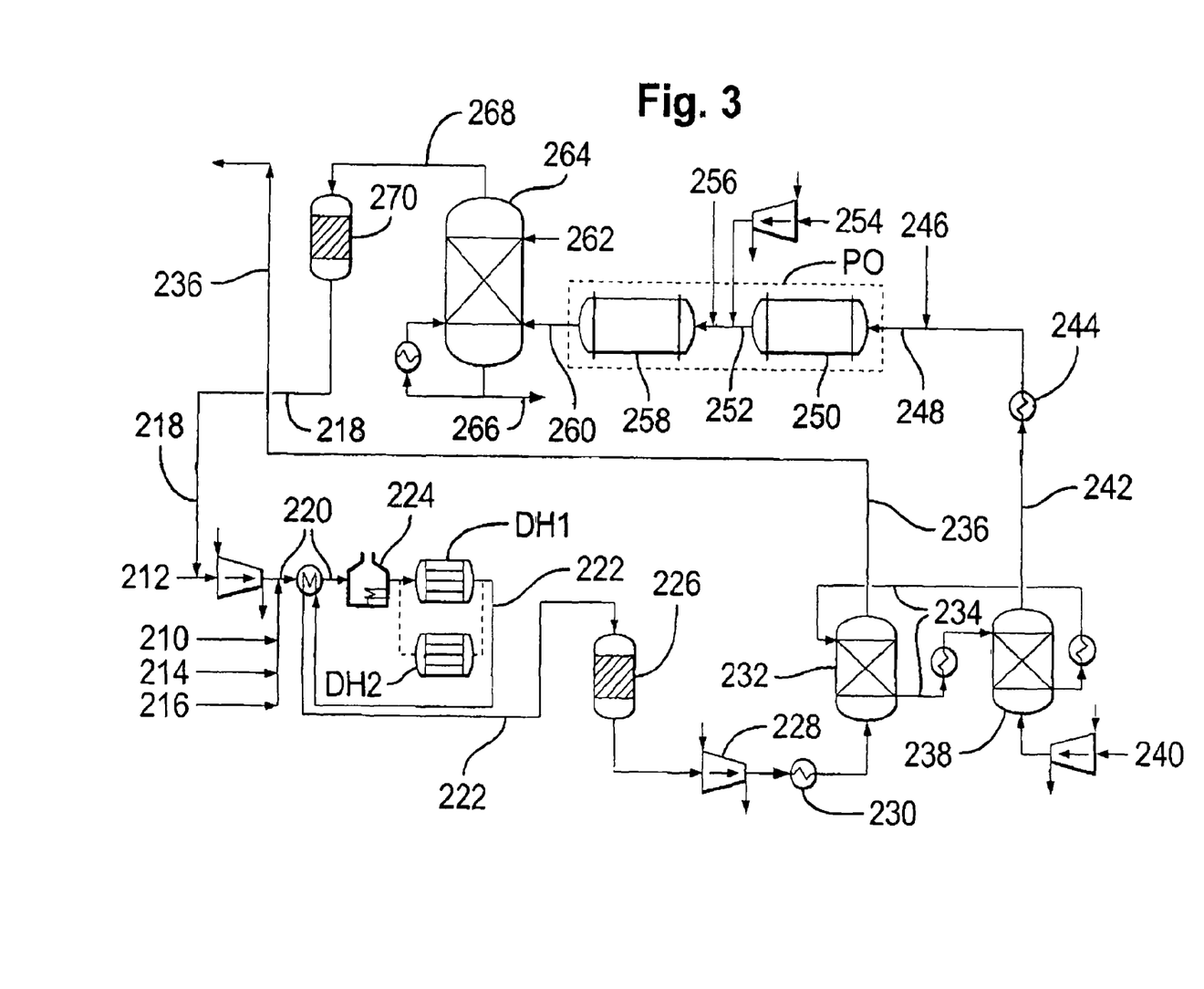
FIG. 3 is a schematic representation of a second particular example of the process of the present invention.

The following description refers to the schematic representation of process equipment shown in FIG. 3. Two dehydrogenations reactors (DH1, DH2), each comprising two reaction zones (not shown per se), are loaded with suitable catalysts (also not shown per se). One reactor at a time is in operation and is used to convert the propane to propene using thermally integrated dehydrogenation processes. When one reactor is not in use, i.e., "off-line," it undergoes catalyst regeneration. The dehydrogenation reactors are automatically cycled on-line and off-line by a process control system (not shown).

The starting materials fed to the oxidative dehydrogenation reaction zones are: propane (210) at 27738 kg/hr, air (212) at 45 m$^3$/min (STP), carbon dioxide (214) at 15211 kg/hr $CO_2$, oxygen (216) at 4160 kg/hr, and 101194 kg/hr recycle gas (218) comprising propane, nitrogen and carbon dioxide, each of the propane, air, and recycle streams (210, 212, 218) having the compositions listed in the following Table 5:

TABLE 5

Feed Composition to Dehydrogenation Reaction Zones

| Component | % (by volume) | | |
|---|---|---|---|
| | Propane | Air | Recycle |
| Propane | 100 | | 33 |
| Nitrogen | | 79 | 19 |
| Oxygen | | 21 | 4 |
| Carbon Dioxide | | | 44 |

The air (212) and recycle gas (218) are combined and compressed to 2.6 bar and combined with the propane (210), $CO_2$ (214) and oxygen (216). The combined propane feed (220) is heated by exchange with the oxidative dehydrogenation reactor effluent (222) to 525° C. and then in a feed heater (224) to the reaction temperature, 625° C.

For each dehydrogenation reactor (DH1, DH2), the first dehydrogenation reaction zone (not shown per se) is loaded with a catalyst (not shown per se) containing 4% V2O5-6% Nb2O5 supported on Davisil 646 for exothermic oxidative dehydrogenation of propane (alkane) to for the corresponding alkene (propene), and the second dehydrogenation reaction zone (not shown per se) is loaded with a catalyst (not shown per se) containing 10% Cr2O3 supported on Merck 10181 for dehydrogenation of additional quantities of propane in the presence of a weak oxidant (i.e., the carbon dioxide), to produce more propene. Contact time in the first dehydrogenation reaction zone is 0.48 sec*ml/g, and the contact time in the second dehydrogenation reaction zone is 0.50 sec*ml/g. To obtain a heat neutral balance between the first and second dehydrogenation zones and, thus, thermally integrated dehydrogenation reaction zones (DH1, DH2), the oxygen concentration in the feed can be adjusted, plus the reactor design must be such that the heat from the first zone exothermic reaction is used provide heat to the second zone endothermic reaction. The composition of the effluent gas (222) from the dehydrogenation reaction zones is provided in the following Table 6:

TABLE 6

Product Stream Composition from Dehydrogenation Reaction Zones

| Component | % (by volume) |
|---|---|
| Carbon Dioxide | 33 |
| Carbon Monoxide | 5 |
| Ethylene | 1 |
| Hydrogen | 6 |
| Methane | 1 |
| Nitrogen | 14 |
| Propane | 25 |
| Propene | 7 |
| Water | 8 |

The cooled effluent gas (222) from the dehydrogenation zones (DH1, DH2) is dried in a molecular sieve dryer (226), compressed (228), and cooled (230) to 10 bar and −37° C. Propane, propene, and $CO_2$ from the effluent gas (222) are absorbed in a solvent, hexane (234). The non-absorbed constituent species (236) can either be incinerated or used as a fuel source. The organic-rich solvent (234) is regenerated in a second column (238) by stripping the propane, propene, and $CO_2$ from the solvent (234) with air (240) at 57 m$^3$/min (STP). The hexane solvent (234) from the regeneration column (238) is recycled back to the absorber (232). The recovered propane, propene, and $CO_2$ (242) is heated (244) to 225° C. and combined with oxygen at 11561 kg/hr and steam at 3362 kg/hr (246). The oxidation reactor feed stream (248) is fed to the first (250) of two partial oxidation zones (PO, 250, 258), at a rate of 112560 kg/hr, and has the composition listed in the following Table 7:

TABLE 7

Feed Stream Composition to Partial Oxidation Reaction Zones

| Component | % (by volume) |
|---|---|
| Carbon Dioxide | 37.7 |
| Nitrogen | 4.2 |
| Oxygen | 13.9 |
| Propane | 28.8 |
| Propene | 8.7 |
| Water | 6.6 |

Propene is converted to acrolein in the first partial oxidation reaction zone (250), in the presence of a mixed metal oxide catalyst containing Mo—W—Bi—Fe—Co—Cs—Si (not shown per se). The acrolein product stream (252) from the first partial oxidation reaction zone (250) is combined with air (254) at 167 m$^3$/min (STP) and steam (256) at 115 kg/hr and fed to the second partial oxidation reaction zone (258), wherein the acrolein is converted to acrylic acid, in the presence of a mixed metal oxide catalyst containing as essential compounds Mo—V—W—Cu—Sb—Ti (not shown per se). Composition of the gaseous effluent (260) from the second partial oxidation reaction zone (258) is as follows:

TABLE 8

Effluent Stream Composition from Partial Oxidation Reaction Zones

| Component | % (by volume) |
|---|---|
| Acetaldehyde | 0.03 |
| Acetic Acid | 0.1 |
| Acrylic Acid | 6.6 |
| Acrolein | 0.03 |
| Carbon Dioxide | 43.3 |
| Nitrogen | 14.7 |

TABLE 8-continued

Effluent Stream Composition from Partial Oxidation Reaction Zones

| Component | % (by volume) |
|---|---|
| Oxygen | 3.3 |
| Propane | 25.5 |
| Propene | 0.2 |
| Water | 15.2 |

The effluent (260) from the partial oxidation reaction zones (PO, 250, 258) is quenched with water (262) in an absorber (264). The aqueous, crude acrylic acid (266) is conducted to separations apparatus (not shown per se) to concentrate the acrylic acid and remove impurities. The gas (268) from the absorber (264) is dried in a molecular sieve dryer (270) and then recycled back to the first oxidation reaction zone (oxidative dehydrogenation) of the oxidation reactors (DH1, DH2). The recycle amount and component composition in the recycle (218) is such that separation of the propane and $CO_2$ is not required.

What is claimed is:

1. A process for producing an unsaturated carboxylic acid or an unsaturated nitrile from the corresponding $C_3$-$C_4$ alkane, said process comprising the steps of:
   A) contacting a $C_3$-$C_4$ alkane and oxygen with an oxidative dehydrogenation catalyst in an exothermic reaction zone, wherein the upstream catalyst is catalytically active for the exothermic conversion of the $C_3$-$C_4$ alkane to its corresponding $C_3$-$C_4$ alkene, in the presence of oxygen; and
   B) exothermically converting a portion of the $C_3$-$C_4$ alkane to the corresponding $C_3$-$C_4$ alkene, in the exothermic reaction zone, to produce a heated mixed product gas which comprises the corresponding $C_3$-$C_4$ alkene, unreacted $C_2$-$C_4$ alkane, and heat produced by said exothermically converting step;
   C) contacting the heated mixed product gas and a weak oxidant comprising carbon dioxide with a endothermic dehydrogenation catalyst in an endothermic reaction zone, wherein the downstream catalyst is catalytically active for the endothermic conversion of the unreacted $C_3$-$C_4$ alkane to the corresponding $C_3$-$C_4$ alkene, in the presence of the weak oxidant comprising carbon dioxide;
   D) endothermically converting at least a portion of the unreacted $C_3$-$C_4$ alkane to the corresponding $C_3$-$C_4$ alkene, in the endothermic reaction zone, to produce a cumulative product stream which comprises at least the corresponding $C_3$-$C_4$ alkene produced in each of the reaction zones;
   E) cooling and drying the cumulative product stream;
   F) separating $C_3$-$C_4$ alkene, unreacted $C_3$-$C_4$ alkane and unreacted carbon dioxide from the cooled cumulative product stream by absorption with a solvent to produce an organic-rich solvent stream comprising the separated $C_3C_4$ alkene, unreacted $C_3$-$C_4$ alkane and unreacted carbon dioxide, and a stream comprising non-absorbed constituents;
   G) separating the $C_3$-$C_4$ alkene, unreacted $C_3$-$C_4$ alkane and unreacted carbon dioxide from the organic-rich solvent stream to produce a recovery stream comprising recovered $C_3$-$C_4$ alkene, $C_3$-$C_4$ alkane and carbon dioxide;
   H) oxidizing the $C_3$-$C_4$ alkene of the recovery stream to produce an oxidation product stream comprising the corresponding unsaturated carboxylic acid or nitrile, in the presence of at least one catalyst capable of facilitating the oxidizing reaction;
   I) separating the oxidation product stream to form an aqueous oxidation product stream comprising the corresponding unsaturated carboxylic acid or nitrile, and a gas stream comprising unreacted $C_3$-$C_4$ alkane and unreacted carbon dioxide;
   J) drying the gas stream and separating the unreacted $C_3$-$C_4$ alkane and unreacted carbon dioxide therefrom; and
   K) recycling the separated unreacted $C_3$-$C_4$ alkane and unreacted carbon dioxide to the exothermic converting step.

2. The process of claim 1, wherein the oxidative dehydrogenation catalyst comprises at least one catalyst composition selected from the group consisting of:
   A) a catalyst comprising one or more noble metals selected from Pt, Pd, Rh, Ir and Ru; and
   B) a catalyst comprising at least one oxide of a metal selected from Li, Mo, W, V, Nb, Sb, Sn, Ga, Zr, Mg, Mn, Ni, Co, Ce and rare earth metals.

3. The process of claim 2, wherein the oxidative dehydrogenation catalyst comprises, as essential materials, vanadium oxide and at least one oxide of a metal selected from the group consisting of: niobium, magnesium, molybdenum and rare earth elements.

4. The process of claim 1, wherein the endothermic dehydrogenation catalyst comprises at least one catalyst composition selected from the group consisting of:
   A) a catalyst comprising chromium oxide and, optionally, oxides of at least one metal selected from the group consisting of Mo, W, V, Ga, Mg, Ni, Fe, alkali elements, alkali earth elements, and rare earth elements;
   B) a catalyst comprising vanadium oxide and, optionally, at least one element selected from the group consisting of Li, Na, K and Mg;
   C) a catalyst comprising platinum and, optionally, at least one metal selected from the group consisting of sodium, potassium, cesium, rhenium and tin; and
   D) a catalyst comprising at least one metal selected from the group consisting of Ga, Fe, Mn and Co.

5. The process of claim 4, wherein the endothermic dehydrogenation catalyst comprises, as essential materials, vanadium oxide, chromium oxide, and at least one metal selected from the group consisting of: copper, silver and gold.

6. The process of claim 1, wherein the $C_3$-$C_4$ alkane comprises propane, and the corresponding $C_3$-$C_4$ alkene comprises propene.

7. The process of claim 1, wherein the separating step G) is performed by stripping with air.

8. The process of claim 1, wherein the oxidizing step H) is performed by a two-step vapor phase catalytic oxidation wherein a first oxidation reaction zone comprises a first oxidation catalyst capable of catalyzing the conversion of the $C_3$-$C_4$ alkene to the corresponding aldehyde, and a second oxidation reaction zone, positioned downstream of the first oxidation reaction zone and comprising a second oxidation catalyst, different from the first oxidation catalyst and capable of catalyzing the conversion of the corresponding aldehyde to the corresponding unsaturated carboxylic acids or nitriles.

9. The process of claim 1, wherein the separating step I) is accomplished by quenching the oxidation product stream with water in an absorber.

10. The process of claim 1, wherein separating the unreacted $C_3$-$C_4$ alkane and unreacted carbon dioxide from the gas stream from the absorber is performed by using a pressure swing absorption system.

* * * * *